(12) United States Patent
Zhong et al.

(10) Patent No.: US 6,426,195 B1
(45) Date of Patent: Jul. 30, 2002

(54) METHOD FOR SILVER STAINING A PATHOLOGIC SAMPLE

(76) Inventors: Shude Zhong, 20395 Summerpark Pl., Castro Valley, CA (US) 94552; Taiying Chen, 9 Elmwood Dr., San Ramon, CA (US) 94583; Sunil Kumar Aggarwal, 2123 Rheem Dr., Pleasanton, CA (US) 94588; Sheng-Hui Su, 2 Craydon Ct., San Ramon, CA (US) 94583

( * ) Notice: Subject to any disclaimer, the term of this patent is extended or adjusted under 35 U.S.C. 154(b) by 0 days.

(21) Appl. No.: 09/538,849

(22) Filed: Mar. 28, 2000

(51) Int. Cl.[7] .............................. C12Q 1/54; G01N 1/30
(52) U.S. Cl. .................. 435/40.5; 435/14; 435/243; 435/4; 435/975; 435/810
(58) Field of Search .................... 435/40.5, 14, 243, 435/4, 975, 283.1, 810

(56) References Cited

U.S. PATENT DOCUMENTS 5,700,656 A * 12/1997 Liu .......................... 435/40.52

* cited by examiner

*Primary Examiner*—Louise N. Leary
(74) *Attorney, Agent, or Firm*—Charles L. Thoeming

(57) ABSTRACT

A method of silver staining a pathologic sample is disclosed. The method involves the reduction of silver diamine complexes bound to components of the sample by a reducing agent released from a reducing agent carrier. The use of a reducing agent carrier which slowly releases the reducing agent during the reaction permits staining at ambient temperatures.

33 Claims, No Drawings

METHOD FOR SILVER STAINING A PATHOLOGIC SAMPLE

TECHNICAL FIELD

This invention relates to a novel method for silver staining a pathologic sample.

BACKGROUND OF THE INVENTION

Humans are subject to a variety of fungal infections, including histoplasmosis, coccidioidomycosis, blastomycosis, paracoccidioidomycosis, sporotrichosis, cryptococcosis, candidiasis, aspergillosis, mucormycosis, mycetoma, chromomycoses and phaeohyphomycosis. Pathogenic fungi are opportunistic pathogens, usually causing disease only in immunocomprised hosts such as the very old, the very young, patients taking immunosuppressive agents, or patients whose immune systems are compromised by another disease or infectious agent. Such patients often show both an increased susceptibility and an increased frequency of fungal infections.

Diagnosis of many fungal infections involves the use of histopathological techniques which permit identification of the fungal pathogen with a high degree of reliability. These techniques allow the identification of the fungal pathogen based on size, morphology and the tissue that it infects. The techniques can be performed on pathologic samples such as tissues obtained from biopsy, autopsy or necropsy, for example from bone marrow, liver biopsy, lymph nodes, oral ulcerations, or infected tissues, or on bodily fluids including sputum, urine, blood, lymph, pleural fluid, cerebrospinal fluid, and exudate from draining lesions. The reliability, accuracy, and reproducibility of the technique used is very important because the identification of the organism involved is critical for diagnosis and treatment. Staining methods in particular are useful both for making the fungal pathogens visible and as diagnostic tools, in that the ability to be visualized with a given stain is characteristic of particular species.

Most fungi are relatively large and their cell walls are rich in polysaccharide. These polysaccharides can be oxidized and the cells walls then visualized using silver staining methods. Grocott's methenamine-silver nitrate procedure ("Histotechnology: A Self-Instructional Text," p. 194–196, F. L. Carson, ASCP Press, Chicago, Ill, 1997) is one silver staining technique used for demonstration of fungal organisms in pathologic samples. The procedure requires several steps of incubation at different temperatures from 56° C. to 60° C. Dilute ammoniacal silver staining techniques such as developed by Churukian et al. (Lab. Med. 17(2):87, 1986) have been used to stain Pneumocystis carinii and fungi using steps requiring a similar temperature range.

The use of caustic, toxic solutions at elevated temperatures complicates the technique and presents a number of safety concerns. Exposure of laboratory personal to hot alkali solutions containing toxic silver is undesirable, and requires additional safety precautions. Manually preparing and maintaining baths at precise temperatures adds to the difficulty of performing the technique and in its reproducibility. Additionally, the need for elevated temperatures at only a few steps of the method complicates automation of the procedures, requiring additional components for raising and monitoring the temperature. This increases the cost of the automated device as well as the space it requires in what are often-crowded laboratories. High temperature incubations can also produce increased background staining and decrease the useful life of staining solutions.

There is a need in the art for a silver staining method which does not require elevated temperatures. Ideally, such a method would be useful in both manual and automated screening procedures. Such a method could be used to detect the presence of fungi, encapsulated bacteria, and other pathogens such as *Pneumocystis carinii,* as well as in place of silver staining techniques used to visualize glycogen, basement membranes, mucins, urate crystals, melanin, or neural components.

SUMMARY OF THE INVENTION

A method is provided that permits silver-staining of a pathologic sample at ambient temperatures. The method involves contacting the sample with a silver diamine complex under basic conditions in the presence of a reducing agent carrier. The method permits staining of sample components which previously were visualized through methods requiring incubation steps at elevated temperatures. The ability to use lower temperatures in the method decreases the exposure of laboratory personnel to the risk of scalding and to fumes produced from hot, toxic solutions. If desired, however, the novel method can also be performed at elevated temperatures as used in previous methods, for example up to about 60° C.

The method of the invention permits intense staining of sample components with low staining background. Fungal spores and hyphae, for example, can be intensively stained with low background at room temperature.

The method therefore does not require preparation of water baths at precise temperatures or control of bath temperatures. Additionally, the method permits automation using devices lacking temperature controls. Devices prepared to perform the method can thus be simpler, with fewer components to maintain and fewer controls to adjust.

In one embodiment, the method involves contacting a pathologic sample with a solution of chromic acid in order to oxidize components of the sample. The sample is then contacted with a basic solution comprising a silver diamine complex and sucrose which results in the depositing of silver metal within the sample. The sample is then treated with a solution of gold chloride, which tones the sample and improves visualization of the stained components. The sample is then treated with a solution of sodium thiosulfate to halt development and to complex with and thereby remove any remaining silver or gold ions. Finally the sample is counterstained by contacting it with a solution of Light Green stain.

A kit comprising reagents useful for performing the method is also provided. In one embodiment the kit comprises an oxidizing agent, a silver diamine complex, a reducing agent carrier and a stopping agent, each of which is received within a housing. A toning agent and a stain can also be included in the kit.

DETAILED DESCRIPTION OF THE INVENTION

A method for silver-staining a pathologic sample which can be performed at ambient temperatures is disclosed. The method involves contacting the sample with a silver diamine complex under basic conditions in the presence of a reducing agent carrier. The reducing agent carrier slowly releases a reducing agent during the course of the reaction, allowing time for the silver diamine complex time to permeate and be localized within the sample prior to reduction of the silver from the complex by the reducing agent. The sample can then be treated with a toning agent, a stopping agent, and a stain to improve visualization. A kit comprising reagents useful for performing the method is also disclosed.

The method of the invention was derived in order to provide a room temperature silver staining technique that could replace Grocott's Methenamine-Silver Nitrate method for staining fungal pathogens, encapsulated bacteria, *Pneumocystis carinii,* glycogen and mucin. Examples of pathogens which can be stained by this method include *Actinomyces israelii, Actinomyces bovis, Aspergillus fumigatus, Blastomyces dermatitidis, Candida albicans, Coccidioides immitis, Cryptococcus neoformans, Histoplasma capsulatum, Nocardia asteroides, Pneumocystis carinii,* and *Sporothrix schenckii.*

The invention can, however, be used in many other types of silver staining methods and can be performed at the elevated temperatures used in previous methods. These methods include, for example, silver impregnation methods (Argentaffin method, Argyrophil method, Churukian and Schenk's argyrophil method, Alcoholic silver nitrate method for argyrophil cells), methods for staining axons and neuronal processes in the central nervous system (Bielschowski's silver stain for axons in frozen and paraffin sections; Marsland, Glees & Erikson's method for axons in paraffin embedded tissues), techniques for staining axons in the peripheral nervous system (Palmgren's method for nerve fibers in paraffin-embedded material; Linder's method for nerves in paraffin sections of soft and mineralized tissue), and methods for staining degenerate nerve fibers (Eager's method for degenerating axons).

Before the present invention is described in detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" includes plural references unless the context clearly dictates otherwise. Thus, for example, reference to "a silver diamine complex" in a sample includes a sample having a plurality of silver diamine complexes, reference to "a reducing agent carrier" includes a plurality of such reducing agent carriers, and the like.

Where a range of values is recited, it is to be understood that each intervening value, to the tenth of the unit of the lower limit of that range, between the recited upper and lower limits of that range is also specifically disclosed, unless the context clearly dictates otherwise. Each smaller range between any recited value or intervening value in a recited range and any other recited or intervening value in that recited range is encompassed within the invention. The upper and lower limits of these smaller ranges can independently be included in or excluded from the range, and each range where either, neither or both limits are included in the smaller range is also encompassed within the invention. Where the recited range includes one or both of the limits, ranges excluding either or both of those included limits are also within the scope of the invention. Where the value being discussed has inherent limits, for example where a component can be present at a concentration of from 0 to 100%, or where the pH of an aqueous solution can range from 1 to 14, those inherent limits as well as any intervening value between an inherent limit and any recited value are specifically disclosed, along with ranges defined by any such value or limit, as described above. Where a value is explicitly recited, it is to be understood that values which are about the same quantity or amount as the recited value are also within the scope of the invention.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

The Sample

The sample is typically a pathologic sample which contains components which can either localize, or be modified to localize, silver diamine complexes within the sample. These components can then be visualized by reduction of the silver ions to silver metal. The sample can be a section of tissue obtained, for example, by surgery or autopsy and processed by histotechnological techniques, or the sample can be a biological specimen such as an aspirate obtained from the lung, a needle biopsy, or a biological fluid such as sputum. The sample can be obtained from any animal species or from deposits left by such animal. The sample can be obtained, for example, from a human or other primate, a mammal, a domesticated animal, for example a cow, horse, goat, llama, alpaca, rabbit, sheep, dog, cat or ferret, a commercially-raised animal, for example an ostrich, buffalo, deer or pig, a pet, for example a fish, bird, reptile, or amphibian, or any animal treated by a veterinarian. The sample can be obtained in a medical or veterinary setting, or can be obtained in the wild.

Sample components which can be visualized using silver staining techniques include polysaccharides. Polysaccharides known to stain using such methods including glycogen, mucin, or components of the cells or cell walls of microbial or opportunistic pathogens. The polysaccharides contained in such samples can be treated with oxidizing agents as described below in order to enhance staining with silver.

The sample can be treated with a fixative prior to performing the silver staining method of the invention. The choice of fixative can be influenced by the type of sample and the particular component to be visualized. Determination of the fixative to be used is within the skill of the art. For example, where a microorganism such as a fungus is to be visualized, the sample is preferably fixed with 10% neutral buffered formalin. Where visualization of tissue containing urate crystals is desired, an absolute alcohol fixative is preferred.

Where the sample is a tissue, the sample is typically sectioned after fixation. The thickness of the section is chosen to permit acceptable visualization of the desired sample component.

Oxidation of the Sample

The sample can be oxidized prior to silver staining in order to increase the staining of desired components to be visualized. Silver staining of some sample components can also be prevented or destroyed by oxidation; this can be advantageous in revealing the staining pattern of other sample components which are unaffected or enhanced by oxidation. Where the sample contains polysaccharide groups, an oxidizing agent can be used to partially oxidize the polysaccharide and generate free aldehyde groups and other oxidized species therein. An oxidizing agent suitable for use in the method can be any agent which can oxidize a component of the sample to produce a desired staining profile while still permitting acceptable visualization. Selection of an oxidizing agent to be used is within the skill of the art. Examples of oxidizing agents useful in the method of the invention include periodic acid and chromic acid. Chromic acid is typically used at a concentration of from about 0.5% to about 10%, preferably at about 5%, at room temperature for a time sufficient to alter the silver staining pattern of the sample without adversely affecting the tissue, typically in the range of about one to about 60 minutes. Examples of other oxidizing agents which can be used include phosphomolybdic acid and potassium permanganate.

Aldehyde groups can also be introduced into the sample through attachment to a probe molecule which binds to a particular portion of the sample. For example, glutaraldehyde can be attached to a probe such as an antibody or oligonucleotide which would then be incubated with the sample so that it binds to the respective antigen or polynucleotide target within the sample, leaving the free aldehyde group on glutaraldehyde available to be detected using the silver staining method described below.

Silver Staining Method

The silver staining method of the invention relies on the reduction of silver ions from a diamine complex to silver metal by aldehyde groups in the sample and from a reducing agent released from a reducing agent carrier. Previous protocols for silver staining fungi require incubations at temperatures from 50° C. to 80° C. This temperature requirement complicates manual staining procedures and prohibits the use of automatic systems which have no controlled-temperature incubating chamber.

The silver diamine complex is a cationic complex formed from a silver cation and two neutral amines. The amines can be ammonia or any organic amine, for example a mono-, di- or tri-lower alkyl- (C1–C6, linear or cyclic) substituted amine, or mixtures thereof, which forms a silver diamine complex that can be used in the method of the invention. Preferably the amine is ammonia. The silver diamine complex can be formed by mixing silver cations with an amine under basic conditions. For example, a silver diamine complex can be formed by mixing silver nitrate with an ammonium hydroxide solution. The pH of the slightly acidic silver nitrate solution rises to 9.5 upon addition of the ammonium hydroxide. Other silver species can deposit under such conditions as the oxide or hydroxide. Ammonium hydroxide is added to drive formation of the diamine complex until these deposits are removed. At that point, further addition of a small amount of ammonium hydroxide will raise the pH to 11–12. If at any point in the method the pH should fall and insoluble nonmetallic silver deposits form, the pH can be raised by adding a suitable base to again solubilize the silver ions as the diamine complex. The silver diamine complex can be used at any concentration that provides acceptable staining of the sample, and can be determined empirically by one of skill in the art. Typically the silver nitrate is added at what would be a final concentration during staining of from about 0.038% to about 38%, preferably at from about 0.38% to about 7%, although the silver is present almost entirely as the amine complex after addition of the amine and elevation of the pH.

The reducing agent carrier can be any substance which allows the release of a reducing agent from the carrier during the silver staining process. The reducing agent can be any agent that reduces silver from the diamine complex, and preferably at ambient temperatures. The carrier preferably releases the reducing agent slowly and continuously during the silver staining process in order to allow the silver diamine complex time to permeate the sample and localize to the areas containing available aldehyde groups and the negatively charged oxidation products produced by oxidation of the aldehyde groups and reduction of silver ions to silver metal. The reducing agent carrier can be, for example, a soluble disaccharide, for example sucrose, lactose, maltose or trehalose, or other reducing sugar derivative which slowly dissociates under the reactions conditions to release a reducing sugar. In a preferred embodiment, the reducing agent carrier is sucrose, which slowly dissociates under the reaction conditions to release the reducing sugar glucose. Any reducing agent carrier which releases a reducing agent during the course of the reaction so that metallic silver is deposited within the sample is within the scope of the invention. In addition to reducing sugars, examples of reducing agents which can be released by the carrier include any molecule which has an available aldehyde group, including lower organic aldehydes such as formaldehyde and acetaldehyde. The reducing agent carrier can be used at any concentration that provides acceptable staining of the sample, and can be determined empirically by one of skill in the art. Typically, where the reducing agent carrier is a disaccharide, it is used at a concentration of from about 0.01% to about 50%, preferably from about 1% to about 40%, and more preferably from about 25% to about 35%.

A working solution comprising both the silver diamine complex and the reducing agent carrier is preferably prepared prior to performing the method and the sample can be introduced into this working solution. The working solution also preferably is sufficiently basic to maintain the solubility of the silver diamine complex. Although impregnation of the sample with the silver diamine complex could take place prior to exposure of the sample to the reducing agent carrier, use of a working solution decreases the total time and number of sample transfers needed to perform the method.

The silver staining reaction is desirably performed in the dark to prevent reduction of silver ions by light. The precise temperature at which the reaction is performed is not critical, but the temperature may affect the reaction rate and the background staining. A suitable temperature is chosen which allows a detectable level of silver staining to occur within a reasonable time (preferably no more than about a few hours, and more preferably about an hour or less) and does not result in unacceptable levels of background staining, which levels can be determined by one of skill in the art. The silver staining method is desirably performed at or about room temperature, which can vary considerably, although the method can also be performed at elevated temperatures found in previous methods. Thus, for example, the method can be performed at a temperature of from about 15° C. to about 60° C., more preferably from about 18° C. to about 35° C., and most preferably from about 20° C. to about 30° C. The method preferably is performed without elevated temperatures in order to prevent exposure of laboratory personnel to hot, caustic solutions and to avoid decreasing the useable lifetime of the reaction solutions and increases in background staining which can occur at elevated temperatures. Lower reaction conditions also permit the use of automated devices which are unable to employ elevated temperatures, and eliminates the need to prepare multiple solutions at different temperatures, thereby simplifying the method.

The pH of the solution is basic in order to maintain the solubility of the silver diamine complex. The pH of the reaction is desirably from about 8 to about 12.5, and is preferably from about 11 to about 12.5. The reaction is allowed to proceed for a sufficient amount of time to permit visualization of the desired component of the sample without causing limiting background staining. Control samples can be included in the reaction and can be removed at various time points and developed to determine the extent of staining.

Toning Step

A toning step whereby the color and stability of the deposited metal are improved can optionally be performed after silver deposition. Toning helps to reduce background staining and increase contrast in the sample. Selection of a toning agent to be used is within the skill of the art. Examples of toning agents which can be used include yellow or brown gold chloride ($AuCl_3$ or $HAuCl_4$), or colloidal gold (Sigma, G1402). The gold ions oxidize the silver metal to soluble silver ions and the gold ions are reduced and deposited as metal. This changes the brown-black deposits produced by the silver staining method into purple-black deposits. The toned gold deposits are more stable than those produced by silver alone and allow for better visualization of the stained sample. Therefore, a toning step is preferred. The toning agent can be used at any concentration that provides acceptable toning of the stained sample, and can be determined empirically by one of skill in the art. Typically the toning agent is used at a concentration of from about 0.02% to about 2%, and preferably at about 0.2%. The pH, temperature and time of the reaction are not critical, and are chosen so as to provide acceptable toning. A suitable pH, temperature and time can be determined by one of skill in the art. Typically, the pH of the reaction is about 2, and the reaction is performed at room temperature for at least 30 seconds.

Stopping Agent

Upon completion of the silver staining method, a stopping agent which prevents deposition of metallic silver or toning agent is used is desirably added. The stopping agent can be any substance which removes unreacted silver or gold cations from the sample without adversely affecting sample visualization. For example, the stopping agent can be a solution of sodium thiosulfate which can form soluble complexes with silver or gold ions and thereby aid in their removal from the sample. Such removal of unreacted metal ions is desirable in order to prevent their reduction upon exposure to light which can increase the background staining in the sample and decrease the ability to visualize the desired components. Typically the toning agent is used at a concentration of from about 0.5% to about 50%, and preferably at about 5%. The pH, temperature and time of the reaction are not critical, and are chosen so as to stop the staining and/or toning from proceeding. A suitable pH, temperature and time can be determined by one of skill in the art. Typically, the pH of the reaction is about 6.75, and the reaction is performed at room temperature for at least 30 seconds.

Rinses

After contacting the sample with any of the foregoing solutions during the method of the invention, it is desirable to rinse the sample before transfer to the next solution. The sample is preferably rinsed a number of times in order to prevent any unreacted solution used in a method step from being transferred. Although it is possible that the sample could be transferred from one solution directly to the next, rinsing is preferred in order to prevent increased background staining and premature solution breakdown. In one embodiment, the rinses are performed with an aqueous solution comprising 0.8% Tween20, 0.02% Antifoam A and distilled water, although other solutions which do not adversely affect the staining method can also be used.

Stains

The silver stained sample can also be treated with another stain that allows visualization of other components of the sample. The stain can be any stain in which does not adversely affect the silver staining method and can, for example, be a stain typically used in conjunction with previous silver staining methods. Examples of stains which can be used include Light Green SF (acid brilliant green, C.I. 42095), Fast Green, hematoxylin and eosin, and nuclear fast red. Typically Light Green is used at a concentration of from about 0.01% to about 1%, and preferably at about 0.1%. Effective staining conditions are known or can be determined by one of skill in the art.

Further Processing

The sample can be subjected to further processing steps prior to analysis. The sample can be dehydrated, for example by treatment with reagent alcohol or a mixture of alcohols, or a graded series of alcohols containing decreasing amounts of water. Preferably, the alcohols are lower alcohols containing from one to six carbons, more preferably from one to four carbons. In one embodiment, a mixture of 5% v/v methyl alcohol, 5% v/v isopropyl alcohol and 90% v/v anhydrous ethyl alcohol is used.

The sample can be cleared, for example by exposure to xylene. Additional staining methods can also be performed. In some instances, it can be desirable to treat the sample so as to remove the effects of prior processing steps, and perform different processing steps incompatible with the steps initially performed. For example, it may be desirable to remove a stain from a given sample and perform a different staining procedure on the sample to visualize a different sample component. Finally, the sample can be mounted with any suitable mounting media. Several mounting media are commercially available, for example Permount™ (Fisher, SP15-100).

Automation of the Method

The silver staining method of the invention can be performed manually or automatically by a device for high throughput analysis. Any device which can perform the silver staining method of the invention can be used, for example the OptiMax®, disclosed in U.S. Pat. No. 5,439,649, or the OptiMax Plus® (U.S. Pat. No. 5,948,359).

An example of the method as performed by the OptiMax Plus® is described below.

Silver Staining Kit

In another embodiment, a silver staining kit is provided. The kit comprises an oxidizing agent, a silver diamine complex, a reducing agent carrier and a stopping agent. The kit components are preferably provided in solution form, but can be provided as solids or in precursor form which can be mixed to provide solutions of the kit components, as where silver nitrate and ammonium hydroxide can be provided for the preparation of the silver diamine complex. The kit can optionally contain other components, for example a toning agent, a stain, a dehydrating solution, and/or mounting media. The kit can comprise other components useful in pathologic methods. Instructions for using the components of the kit in the method of the invention can also be provided, and can be supplied in any fixed medium, for example in writing or on CD-ROM, audiotape, CD, DVD or videotape. The components of the kit are provided inside a housing that allows convenient transport and storage.

EXAMPLES

The following example is set forth so as to provide those of ordinary skill in the art with a complete description of how to make and use one embodiment of the present invention, and is not intended to limit the scope of what is regarded as the invention. Unless indicated otherwise, parts are parts by weight, temperature is degree centigrade and pressure is at or near atmospheric.

Example 1.

Silver Staining Method for Fungi

This example describes the staining of fungi within a pathologic sample using the method of the invention. This embodiment was developed in order to provide a silver staining method for fungi to replace Grocott's Methenamine Silver-staining procedure, which includes high temperature incubations. The method is an automated procedure designed for use with the OptiMax Plus® (BioGenex Laboratories, Inc., San Ramon, Calif.).

Polysaccharides in the fungal cell wall can be oxidized with chromic acid. Chromic acid is a strong oxidant, producing aldehyde groups from polysaccharides in the sample as well as further breakdown products, which helps suppress the weaker silver staining that can occur with collagen fibers and basement membranes. Only substances that possess large quantities of polysaccharides, such as fungal cell walls, glycogen, and mucins, remain reactive with silver after such strong oxidation.

The sample is contacted with an ammoniacal silver solution. During this step, ammoniacal or diamine silver complexes $[Ag(NH_3)_2]^+$ are localized within the sample. Sucrose, functioning as reducing agent carrier, slowly breaks down in this basic solution to fructose and the reducing sugar glucose. This applies a slow and continuous reducing effect that allows the diamine silver complexes to diffuse into the oxidized fungal cell wall before reduction to metallic silver.

Fixation plays an important role in preserving the tissue structures to be visualized using this method. 10% neutral buffered formalin is preferred. Tissue sections should be mounted on positive-charged slides and dried in a 50° C. oven overnight. Cut tissue sections to 4–5 microns.

Samples prepared in this manner were stained with silver using the following protocol. Barcoded reagent vials containing the solutions listed below were obtained from BioGenex Laboratories, San Ramon, Calif. Dewaxing was performed with EZ-DeWax™ solution (HK585-5K, BioGenex Laboratories, San Ramon, Calif). GMS Working Solution was prepared by adding an equal volume of GMS Silver Stock Solution (HK743-05K, BioGenex Laboratories, Inc.) to one vial of GMS Silver Diluent (HK742-10X, BioGenex Laboratories, Inc.), and mixing well. GMS Silver Stock Solution contains 7.6% silver nitrate and 4.2% ammonium hydroxide. GMS Silver Diluent solution contains 30% sucrose and 1.54% potassium hydroxide. Chromic acid solution contains 5% chromic acid (HK780-20X, BioGenex Laboratories, Inc.). Reagent Alcohol contains 90% ethanol, 5% methanol and 5% isopropanol (HK723-20X, BioGenex Laboratories, Inc.). Light Green Solution was prepared by dissolving 0.1 gram of Light Green SF yellowish in 70 mls of Reagent Alcohol, and distilled water was added to bring the volume to 100 ml. (HK722-20X, BioGenex Laboratories, Inc.). The reagents were stored at 2–8° C. until use. Rinses were performed with Special Stains Wash Solution (0.8% Tween20 and 0.2% Antifoam A in distilled water) made from a 20X stock (HK755-5K, BioGenex Laboratories, Inc.)

OptiMax® Plus Staining Protocol
1. Bring reagents to room temperature before use.
2. Load the barcode-labeled slides for the appropriate stain into the OptiMax Plus® slide racks. Load the barcode-labeled reagent vials into the OptiMax Plus® reagent racks.
3. Start the Special Stains software on the instrument and check the protocol parameters against the factory default settings listed below. Change any of the parameters as required. Note that any parameter change, once saved, becomes the default setting until changed again. Use of parameter settings other than the factory defaults requires validation by the user.
4. Select "Start Scan" and the instrument will perform the steps listed in the table (if the factory default settings have been selected).
5. After staining, dehydrate the slides directly in 100% alcohol, clear in xylene, and apply permanent mounting medium.

GMS Protocol Default Setting

| Reagent | No. of Incubations | Incubation Time | No. of After Rinses |
| --- | --- | --- | --- |
| DeWax | 2 | 3 min. | 4 |
| Chromic Acid | 1 | 30 min. | 5 |
| GMS Working Solution | 2* | 14 min. | 3 |
| 0.2% Gold Chloride | 1 | 5 min. | 3 |
| 5% Sodium Thiosulfate | 1 | 2 min. | 3 |
| Light Green | 1 | 2 min. | 0 |
| 100% Reagent Alcohol | 1 | 1 min. | 0 |

*There is one rinse between the two incubations.

Recommended Parameter Settings (Default)

| Dewax: Yes | Pre-Wash: No |
| --- | --- |
| Reagent Vol.: 200 µl | Dispensing Pattern: 2/3 |

Dewax Incubation Time: 3 min.

Results

Fungi were stained black with a light green background.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. A method for silver staining a pathologic sample, comprising contacting the sample under basic conditions with a silver diamine complex and a reducing agent carrier, whereby the reducing agent released by the carrier reduces silver from the diamine complex, thereby depositing $Ag^0$ in the sample.

2. The method of claim 1, wherein the sample is treated with an oxidizing agent prior to silver staining.

3. The method of claim 2, wherein the oxidizing agent is chromic acid.

4. The method of claim 1, wherein the silver diamine complex is formed by mixing silver nitrate with a solution of ammonium hydroxide.

5. The method of claim 1, wherein the silver diamine complex is formed by mixing silver nitrate with a solution of an organic amine.

6. The method of claim 5, wherein the organic amine is methylamine.

7. The method of claim 1, wherein the reducing agent carrier comprises a reducing sugar.

8. The method of claim 7, wherein the reducing sugar is glucose.

9. The method of claim 8, wherein the reducing agent carrier is a disaccharide.

10. The method of claim 9, wherein the disaccharide is sucrose.

11. The method of claim 1, wherein the silver in the diamine complex is reduced at a temperature from about 15° C. to about 60° C.

12. The method of claim 11, wherein the silver in the diamine complex is reduced at a temperature from about 18° C. to about 35° C.

13. The method of claim 12, wherein the silver in the diamine complex is reduced at a temperature from about 20° C. to about 30° C.

14. The method of claim 1, wherein the sample is a tissue sample.

15. The method of claim 1, wherein the sample comprises a microorganism.

16. The method of claim 15, wherein the microorganism stained is selected from the group consisting of *Actinomyces israelii, Actinomyces bovis, Aspergillus fumigatus, Blastomyces dermatitidis, Candida albicans, Coccidioides immitis, Cryptococcus neoformans, Histoplasma capsulatum, Nocardia asteroides, Pneumocystis carinii,* and *Sporothrix schenckii.*

17. The method of claim 15, wherein the microorganism is an encapsulated bacterium.

18. The method of claim 15, wherein the microorganism is a yeast.

19. The method of claim 1, wherein the sample comprises glycogen.

20. The method of claim 1, wherein the sample comprises a mucin.

21. The method of claim 1, further comprising rinsing the sample after $Ag^0$ is deposited.

22. The method of claim 21, further comprising contacting the sample with a toning agent after rinsing the sample.

23. The method of claim 22, wherein the toning agent comprises gold chloride.

24. The method of claim 1, further comprising contacting the sample with a reaction termination agent.

25. The method of claim 24, wherein the reaction termination agent comprises sodium thiosulfate.

26. The method of claim 24, further comprising contacting the sample with a counter-stain.

27. The method of claim 26, wherein the counter-stain is Light Green.

28. The method of claim 26, further comprising contacting the sample with a dehydrating agent.

29. The method of claim 28, wherein the dehydrating agent consists of a mixture of lower alcohols.

30. The method of claim 1, wherein the method is performed by an automated device.

31. A method of silver staining a sample, comprising contacting the sample in the following order with:
    a solution of chromic acid;
    a washing solution;
    a basic solution comprising silver diamine complex and sucrose;
    a washing solution;
    a solution of gold chloride;
    a washing solution;
    a solution of sodium thiosulfate;
    a washing solution; and
    a Light Green staining solution.

32. A silver staining kit comprising:
    an oxidizing agent,
    a silver diamine complex,
    a reducing agent carrier, and
    a reaction termination agent,
    each of which is received within a housing.

33. The kit of claim 32, further comprising a toning agent and a counter-stain received within the housing.

* * * * *

UNITED STATES PATENT AND TRADEMARK OFFICE
CERTIFICATE OF CORRECTION

PATENT NO. : 6,426,195 B1  Page 1 of 1
DATED : July 30, 2002
INVENTOR(S) : Shude Zhong et al.

It is certified that error appears in the above-identified patent and that said Letters Patent is hereby corrected as shown below:

Column 2,
Lines 53 and 67, delete "stopping" and substitute -- reaction termination --.
Line 54, delete "stain" and substitute -- counter-stain --.

Column 3,
Line 1, delete "stain" and substitute -- counter-stain --.

Column 7,
Line 37, delete "Stopping" and substitute -- Reaction Termination --.
Lines 38, 40 and 43, delete "stopping" and substitute -- reaction termination --.

Column 8,
Line 6, delete "Stains" and substitute -- Counter-stains --.
Line 8, delete "stain" and substitute -- counter-stain --.
Line 9, delete the first occurrence of "stain" and substitute -- counter-stain --.
Line 12, delete "stains" and substitute -- counter-stains --.
Line 17, delete "staining" and substitute -- counter-staining --.
Line 47, after "(U.S. Pat. No. 5,948,359) insert -- , or the i1600—™ (Patent Pending) --.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,426,195 B1  
DATED        : July 30, 2002  
INVENTOR(S)  : Shude Zhong et al.

It is certified that error appears in the above-identified patent and that said Letters Patent is hereby corrected as shown below:

Column 2,  
Line 53, delete "stopping" and substitute -- reaction termination --.  
Line 54, delete "stain" and substitute -- counter-stain --.  
Line 67, delete "stopping" and substitute -- reaction termination --.

Column 3,  
Line 1, delete "stain" and substitute -- counter-stain --.

Column 7,  
Line 37, delete "Stopping" and substitute -- Reaction Termination --.  
Lines 38, 40 and 43, delete "stopping" and substitute -- reaction termination --.

Column 8,  
Line 6, delete "Stains" and substitute -- Counter-stains --.  
Line 8, delete "stain" and substitute -- counter-stain --.  
Line 9, delete the first occurrence of "stain" and substitute -- counter-stain --.  
Line 12, delete "stains" and substitute -- counter-stains --.  
Line 17, delete "staining" and substitute -- counter-staining --.  
Line 47, after "U.S. Pat. No. 5,948,359" insert -- , or the i1600—$^{TM}$ (Patent Pending) --.

Signed and Sealed this

Second Day of September, 2003

JAMES E. ROGAN  
*Director of the United States Patent and Trademark Office*

UNITED STATES PATENT AND TRADEMARK OFFICE
CERTIFICATE OF CORRECTION

PATENT NO. : 6,426,195 B1 Page 1 of 1
DATED : July 30, 2002
INVENTOR(S) : Zhong et al.

It is certified that error appears in the above-identified patent and that said Letters Patent is hereby corrected as shown below:

<u>Title page,</u>
Item [76], after Inventors, insert
-- [73] Assignee: BioGenex Laboratories, Inc., 4600 Norris Canyon Road, San Ramon, California 94583. --

Signed and Sealed this

Fourth Day of November, 2003

JAMES E. ROGAN
*Director of the United States Patent and Trademark Office*